United States Patent [19]
Lee et al.

[11] Patent Number: 5,770,444
[45] Date of Patent: Jun. 23, 1998

[54] GROWTH DIFFERENTIATION FACTOR-6

[75] Inventors: Se-Jin Lee; Thanh Huynh, both of Baltimore, Md.

[73] Assignee: The Johns Hopkins University School of Medicine, Baltimore, Md.

[21] Appl. No.: 581,529

[22] PCT Filed: Jul. 8, 1994

[86] PCT No.: PCT/US94/07762

§ 371 Date: Apr. 15, 1996

§ 102(e) Date: Apr. 15, 1996

[87] PCT Pub. No.: WO95/01601

PCT Pub. Date: Jan. 19, 1995

Related U.S. Application Data

[63] Continuation of Ser. No. 89,300, filed as PCT/US94/07762 Jul. 8, 1994, abandoned.

[51] Int. Cl.[6] .......................... C07K 14/475; C12N 1/19; C12N 5/10; C12N 15/12
[52] U.S. Cl. .................. 435/325; 435/172.3; 435/252.3; 435/320.1; 530/350; 530/397; 530/399; 536/23.1; 536/23.5; 536/23.51; 536/24.3; 536/24.31
[58] Field of Search ..................................... 530/350, 397, 530/399; 435/69.1, 69.4, 172.3, 240.1, 252.3, 320.1, 325; 536/23.1, 235, 23.51, 24.3, 24.31

[56] References Cited

PUBLICATIONS

Bowie et al. Science 247:1306–10, 1990.
Rudinger Peptide Hormones, Parsons, ed., University Park Press, Baltimore, pp. 1–7, 1976.
Wells, Biochemistry 29:8509–17, 1990.
Ngo et al. The Protein Folding Problem and tertiary Structure Prediction, Merz et al., eds., Birkhauser, Boston, pp. 491–495, 1994.
Massague, Cell 49:437–8, 1987.
Callard et al. The Cytokine FatsBook, Academic Press, London, pp. 31–2, 1994.

*Primary Examiner*—Elizabeth C. Kemmerer
*Attorney, Agent, or Firm*—Fish & Richardson, P.C.

[57] ABSTRACT

Growth differentiation factor-6 (GDF-6) polypeptides, polynucleotides encoding GDF-6 polypeptides, and vectors and host cells containing GDF-6 encoding polynucleotides are provided.

11 Claims, 4 Drawing Sheets

```
  1 GCCCTGCTTGTAGTGTTCACCAGATCGCCAGCGCAAGAACCTGTTCACTGAGATGCATGAG   60
 61 CAGCTGGGCTCTGCAGAGGCTGGCGGGAGCCGAGGGGTCATGGCCGCCGTCGGGCTCC    120
121 CAGACGCCGGGTCTTGGCTGCCCTCGCCCGCCGGCGCCGACGCCCTTCGCCA           180
     A  G  S  W  L  P  S  P  G  R  R  R  R  T  A  F  S
181 GCCGTCACGGCAAGCGGACGGACAATGGGCAAGAAGTCCAGGCTGCGCTGCAGCAGAAAGCCTCTGC  240
     R  H  G  K  R  H  G  K  K  S  R  L  R  C  S  R  K  P  L  H
241 ACGTGAATTTTAAGGAGCTGGGACGACTGGGATTATCGCGCCCCTAGAGTACGAGG       300
     V  N  F  K  E  L  G  W  D  D  W  I  A  P  L  E  Y  E  A
301 CCTATCACTGCGAGGGCGTGTGCGACTTTCCGCTCGCCACCTTGAGCCACTAACC       360
     Y  H  C  E  G  V  C  D  F  P  L  R  S  H  L  E  P  T  N  H
361 ATGCCATCATTCAGACGCTGATGAACTCCATGGACCCGGGCTCCACCCCGCCTAGCTGCT  420
     A  I  Q  T  L  M  N  S  M  D  P  G  S  T  P  P  S  C  C
421 GCGTTCCCACCAAACTGACTCCCATTAGCATCCTGTACATCGACGCGGGCAATAATGTAG  480
     V  P  T  K  L  T  P  I  S  I  L  Y  I  D  A  G  N  N  V  V
481 TCTACAAGCAGTATGAGGACATGGTGGTGGAGTCCTGCGGGCTGTGTAGGTAG   530
     Y  K  Q  Y  E  D  M  V  V  E  S  C  G  C  R  *
```

FIG. 2

```
GDF-6        AFASRHGKRHGKKSRLRCSRKPLHVNF-KELGWDDWIIAPLEYEAYHCEGVCDFPLRSHLEP----
GDF-1        RPRRDAEPVLGGGPGGACRARRLYVSF-REVGWHRWVIAPRGFLANYCQGQCALPVALSGSGGPP
BMP-2        REKRQAKHKQRKRLKSSCKRHPLYVDF-SDVGWNDWIVAPPGYHAFYCHGECPFPLADHLNS---
BMP-4        KRSPKHHSQRARKKNKNCRRHSLYVDF-SDVGWNDWIVAPPGYQAFYCHGDCPFPLADHLNS---
Vgr-1        SRGSGSSDYNGSELKTACKKHELYVSF-QDLGWQDWIIAPKGYAANYCDGECSFPLNAHMNA---
OP-1         LRMANVAENSSSDQRQACKKHELYVSF-RDLGWQDWIIAPEGYAAYYCEGECAFPLNSYMNA---
BMP-5        SRMSSVGDYNTSEQKQACKKHELYVSF-RDLGWQDWIIAPEGYAAFYCDGECSFPLNAHMNA---
BMP-3        EQTLKKARRKQWIEPRNCARRYLKVDF-ADIGWSEWIISPKSFDAYYCSGACQFPMPKSLKPS--
MIS          GPGRAQRSAGATAADGPCALRELSVDL----RAERSVLIPETYQANNCQGVCGWPQSDRNPRY--
Inhibin α    ALRLLQRPPEEPAAHANCHRVALNISF-QELGWERWIVYPPSFIFHYCHGGCGLHIPPNLSLPV-
Inhibin βA   HRRRRGLECDGKV-NICCKKQFFVSF-KDIGWNDWIIAPSGYHANYCEGECPSHIAGTSGSSL-
Inhibin βB   HRIRKRGLECDGRT-NLCCRQQFFIDF-RLIGWNDWIIAPTGYYGNYCEGSCPAYLAGVPGSAS-
TGF-β1       HRRALDTNYCFSSTEKNCCVRQLYIDFRKDLGW-K-WIHEPKGYHANFCLGPCPYIWSLD-----
TGF-β2       KKRALDAAYCFRNVQDNCCLRPLYIDFKRDLGW-K-WIHEPKGYNANFCAGACPYLWSSD-----
TGF-β3       KKRALDTNYCFRNLEENCCVRPLYIDFRQDLGW-K-WVHEPKGYYANFCSGPCPYLRSAD-----

GDF-6        -TNHAIIQTLMNS--MDPGSTPPSCCV--PTKLTPISILYI-DAGNNVVYKQYEDMVVESCGCR
GDF-1        ALNHAVLRALMHA--AAPGAADLPCCV--PARLSPISVLFF-DNSDNVVLRQYEDMVVDECGCR
BMP-2        -TNHAIVQTLVNS---VNSKIPKACCV--PTELSAISMLYL-DENEKVVLKNYQDMVVEGCGCR
BMP-4        -TNHAIVQTLVNS---VNSSIPKACCV--PTELSAISMLYL-DEYDKVVLKNYQEMVVEGCGCR
Vgr-1        -TNHAIVQTLVHL---MNPEYVPKPCCA--PTKLNAISVLYF-DDNSNVVILKKYRNMVVRACGCH
OP-1         -TNHAIVQTLVHL---INPETVPKPCCA--PTQLNAISVLYF-DDSSNVILKKYRNMVVRACGCH
BMP-5        -TNHAIVQTLVHL---MFPDHVPKPCCA--PTQLNAISVLYF-DDSSNVILKKYRNMVRSCGCH
BMP-3        -NHATIQSIVRA-VGVVPGIPEPCCV--PEKMSSLSILFF-DENKNVVLKVYPNMTVESCACR
MIS          -GNHVVLLLKMQA--RGAALARPPCCV--PTAYAGKLLISLSEER--ISAHHVPNMVATECGCR
Inhibin α    -PGAPPTPAQPYS---LLPGAQPCQAALPGTMRPLHVRTTSDGGYSFKYETVPNLLTQHCACI
Inhibin βA   -SFHSTVINHYRMRGHSPFANLKSCCV--PTKLRPMSMLYY-DDGQNIIKKDIQNMIVEECGCS
Inhibin βB   -SFHTAVVNQYRMRGLNPGT-VNSCCI--PTKLSTMSMLYF-DDEYNIVKRDVPNMIVEEGCA
TGF-β1       -TQYSKVLALYNQ--HNPGASAAPCCV--PQALEPLPIVYY-VGRKPKV-EQLSNMIVRSCKCS
TGF-β2       -TQHSRVLSLYNT--INPEASASPCCV--SQDLEPLTILYY-IGKTPKI-EQLSNMIVKSKCS
TGF-β3       -TTHSTVLGLYNT--LNPEASASPCCV--PQDLEPLTILYY-VGRTPKV-EQLSNMVVKSCKCS
```

| | GDF-1 | GDF-2 | GDF-3 | GDF-5 | GDF-6 | GDF-7 | GDF-8 | GDF-9 | BMP-2 | BMP-4 | Vgr-1 | OP-1 | BMP-5 | BMP-3 | MIS | Inhibin α | Inhibin βA | Inhibin βB | TGF-β1 | TGF-β2 | TGF-β3 |
|---|---|---|---|---|---|---|---|---|---|---|---|---|---|---|---|---|---|---|---|---|---|
| TGF-β3 | 33 | 33 | 30 | 32 | 37 | 38 | 38 | 37 | 25 | 36 | 35 | 39 | 38 | 36 | 32 | 25 | 24 | 37 | 36 | 78 | 82 |
| TGF-β2 | 32 | 32 | 28 | 31 | 34 | 36 | 35 | 37 | 25 | 34 | 33 | 37 | 38 | 35 | 32 | 23 | 22 | 37 | 34 | 74 | 100 |
| TGF-β1 | 33 | 26 | 36 | 33 | 35 | 36 | 34 | 34 | 23 | 35 | 34 | 35 | 34 | 32 | 28 | 23 | 41 | 35 | 100 | – | – |
| Inhibin βB | 35 | 25 | 41 | 37 | 39 | 36 | 42 | 31 | 42 | 42 | 41 | 42 | 37 | 37 | 25 | 25 | 63 | 100 | – | – | – |
| Inhibin βA | 37 | 32 | 42 | 40 | 43 | 41 | 38 | 30 | 42 | 41 | 44 | 43 | 43 | 36 | 24 | 26 | 100 | – | – | – | – |
| Inhibin α | 23 | 20 | 25 | 24 | 27 | 26 | 26 | 27 | 22 | 22 | 25 | 24 | 24 | 29 | 18 | 100 | – | – | – | – | – |
| MIS | 34 | 20 | 22 | 27 | 26 | 25 | 31 | 21 | 27 | 27 | 24 | 27 | 24 | 30 | 100 | – | – | – | – | – | – |
| BMP-3 | 42 | 34 | 42 | 47 | 46 | 46 | 38 | 29 | 48 | 47 | 44 | 42 | 43 | 100 | – | – | – | – | – | – | – |
| BMP-5 | 46 | 55 | 50 | 52 | 54 | 52 | 42 | 31 | 61 | 59 | 91 | 88 | 100 | – | – | – | – | – | – | – | – |
| OP-1 | 47 | 52 | 50 | 51 | 53 | 53 | 42 | 30 | 60 | 58 | 87 | 100 | – | – | – | – | – | – | – | – | – |
| Vgr-1 | 46 | 55 | 53 | 51 | 53 | 52 | 45 | 31 | 61 | 60 | 100 | – | – | – | – | – | – | – | – | – | – |
| BMP-4 | 43 | 51 | 50 | 57 | 56 | 57 | 38 | 34 | 92 | 100 | – | – | – | – | – | – | – | – | – | – | – |
| BMP-2 | 42 | 52 | 53 | 57 | 57 | 57 | 41 | 33 | 100 | – | – | – | – | – | – | – | – | – | – | – | – |
| GDF-9 | 27 | 32 | 33 | 33 | 34 | 33 | 27 | 100 | – | – | – | – | – | – | – | – | – | – | – | – | – |
| GDF-8 | 35 | 31 | 41 | 37 | 38 | 37 | 100 | – | – | – | – | – | – | – | – | – | – | – | – | – | – |
| GDF-7 | 48 | 48 | 46 | 80 | 80 | 100 | – | – | – | – | – | – | – | – | – | – | – | – | – | – | – |
| GDF-6 | 44 | 51 | 49 | 86 | 100 | – | – | – | – | – | – | – | – | – | – | – | – | – | – | – | – |
| GDF-5 | 46 | 47 | 49 | 100 | – | – | – | – | – | – | – | – | – | – | – | – | – | – | – | – | – |
| GDF-3 | 50 | 42 | 100 | – | – | – | – | – | – | – | – | – | – | – | – | – | – | – | – | – | – |
| GDF-2 | 33 | 100 | – | – | – | – | – | – | – | – | – | – | – | – | – | – | – | – | – | – | – |
| GDF-1 | 100 | – | – | – | – | – | – | – | – | – | – | – | – | – | – | – | – | – | – | – | – |

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: SJL141

( i x ) FEATURE:
        ( A ) NAME/KEY: CDS
        ( B ) LOCATION: 1..35
        ( D ) OTHER INFORMATION: /note= "V=guanine, cytosine or adenine; N=adenine, cytosine, guanine or thymine; R=adenine or guanine; Y=cytosine or thymine; K=thymine or guanine; N=inosine"

( x i ) SEQUENCE DESCRIPTION: SEQ ID NO:1:

CCGGAATTCG GNTGGVANRA YTGGRTNRTN KCNCC 35

(2) INFORMATION FOR SEQ ID NO:2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: SJL145

(ix) FEATURE:
        (A) NAME/KEY: CDS
        (B) LOCATION: 1..29
        (D) OTHER INFORMATION: /note= "R=adenine or guanine;
            S=cytosine or guanine; M=adenine or cytosine;
            N=adenine, cytosine, guanine or thymine;
            Y=cytosine or thymine; N=inosine"

(xi) SEQUENCE DESCRIPTION: SEQ ID NO:2:

CCGGAATTCR CANSCRCANG MNTCNACNRY CAT 33

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: SJL141

(ix) FEATURE:
        (A) NAME/KEY: Peptide
        (B) LOCATION: 1..9
        (D) OTHER INFORMATION: /note= "Xaa at position 3=His, Gln,
            Asn, Lys, Asp or Glu; Xaa at position 4=Asp or
            Asn; Xaa at positions 6 and 7=Val, Ile or Met;
            Xaa at position 8=Ala or Ser"

(xi) SEQUENCE DESCRIPTION: SEQ ID NO:3:

Gly Trp Xaa Xaa Trp Xaa Xaa Xaa Pro
1                 5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (B) CLONE: SJL145

(ix) FEATURE:
        (A) NAME/KEY: Peptide
        (B) LOCATION: 1..8
        (D) OTHER INFORMATION: /note= "Xaa at position 2=Val,
            Ile, Met, Thr or Ala; Xaa at position 4=Asp or Glu;
            Xaa at position 5=Ala or Ser; Xaa at position 6=Gly
            or Ala"

(xi) SEQUENCE DESCRIPTION: SEQ ID NO:4:

```
    Met  Xaa  Val  Xaa  Xaa  Cys  Xaa  Cys
      1              5
```

(2) INFORMATION FOR SEQ ID NO:5:

(i) SEQUENCE CHARACTERISTICS:
        (A) LENGTH: 530 base pairs
        (B) TYPE: nucleic acid
        (C) STRANDEDNESS: single
        (D) TOPOLOGY: linear (ii) MOLECULE TYPE: DNA (genomic)

(vii) IMMEDIATE SOURCE:
        (B) CLONE: GDF-6

(ix) FEATURE:
        (A) NAME/KEY: CDS
        (B) LOCATION: 126..527

(xi) SEQUENCE DESCRIPTION: SEQ ID NO:5:

```
GCCCTGCTTG  TAGTGTTCAC  CAGATCGCAG  CGCAAGAACC  TGTTCACTGA  GATGCATGAG         60

CAGCTGGGCT  CTGCAGAGGC  TGCGGGAGCC  GAGGGGTCAT  GGCCAGCGCC  GTCGGGCTCC        120

CAGAC  GCC  GGG  TCT  TGG  CTG  CCC  TCG  CCC  GGC  CGC  CGG  CGG  CGA  CGC   167
       Ala  Gly  Ser  Trp  Leu  Pro  Ser  Pro  Gly  Arg  Arg  Arg  Arg  Arg
         1              5                        10

ACC  GCC  TTC  GCC  AGC  CGT  CAC  GGC  AAG  CGA  CAT  GGC  AAG  AAG  TCC  AGG  215
Thr  Ala  Phe  Ala  Ser  Arg  His  Gly  Lys  Arg  His  Gly  Lys  Lys  Ser  Arg
 15                  20                       25                          30

CTG  CGC  TGC  AGC  AGA  AAG  CCT  CTG  CAC  GTG  AAT  TTT  AAG  GAG  TTA  GGC  263
Leu  Arg  Cys  Ser  Arg  Lys  Pro  Leu  His  Val  Asn  Phe  Lys  Glu  Leu  Gly
                    35                       40                          45

TGG  GAC  GAC  TGG  ATT  ATC  GCG  CCC  CTA  GAG  TAC  GAG  GCC  TAT  CAC  TGC  311
Trp  Asp  Asp  Trp  Ile  Ile  Ala  Pro  Leu  Glu  Tyr  Glu  Ala  Tyr  His  Cys
               50                       55                           60

GAG  GGC  GTG  TGC  GAC  TTT  CCG  CTG  CGC  TCG  CAC  CTT  GAG  CCC  ACT  AAC  359
Glu  Gly  Val  Cys  Asp  Phe  Pro  Leu  Arg  Ser  His  Leu  Glu  Pro  Thr  Asn
          65                       70                            75

CAT  GCC  ATC  ATT  CAG  ACG  CTG  ATG  AAC  TCC  ATG  GAC  CCG  GGC  TCC  ACC  407
His  Ala  Ile  Ile  Gln  Thr  Leu  Met  Asn  Ser  Met  Asp  Pro  Gly  Ser  Thr
      80                       85                            90

CCG  CCT  AGC  TGC  TGC  GTT  CCC  ACC  AAA  CTG  ACT  CCC  ATT  AGC  ATC  CTG  455
Pro  Pro  Ser  Cys  Cys  Val  Pro  Thr  Lys  Leu  Thr  Pro  Ile  Ser  Ile  Leu
 95                 100                      105                        110

TAC  ATC  GAC  GCG  GGC  AAT  AAT  GTA  GTC  TAC  AAG  CAG  TAT  GAG  GAC  ATG  503
Tyr  Ile  Asp  Ala  Gly  Asn  Asn  Val  Val  Tyr  Lys  Gln  Tyr  Glu  Asp  Met
                    115                      120                        125

GTG  GTG  GAG  TCC  TGC  GGC  TGT  AGG  TAG                                    530
Val  Val  Glu  Ser  Cys  Gly  Cys  Arg
                130
```

(2) INFORMATION FOR SEQ ID NO:6:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:6:

```
Ala  Gly  Ser  Trp  Leu  Pro  Ser  Pro  Gly  Arg  Arg  Arg  Arg  Arg  Thr  Ala
  1              5                        10                           15

Phe  Ala  Ser  Arg  His  Gly  Lys  Arg  His  Gly  Lys  Lys  Ser  Arg  Leu  Arg
                20                       25                           30
```

```
Cys  Ser  Arg  Lys  Pro  Leu  His  Val  Asn  Phe  Lys  Glu  Leu  Gly  Trp  Asp
          35                       40                       45

Asp  Trp  Ile  Ile  Ala  Pro  Leu  Glu  Tyr  Glu  Ala  Tyr  His  Cys  Glu  Gly
          50                       55                       60

Val  Cys  Asp  Phe  Pro  Leu  Arg  Ser  His  Leu  Glu  Pro  Thr  Asn  His  Ala
65                       70                       75                       80

Ile  Ile  Gln  Thr  Leu  Met  Asn  Ser  Met  Asp  Pro  Gly  Ser  Thr  Pro  Pro
               85                       90                       95

Ser  Cys  Cys  Val  Pro  Thr  Lys  Leu  Thr  Pro  Ile  Ser  Ile  Leu  Tyr  Ile
               100                      105                      110

Asp  Ala  Gly  Asn  Asn  Val  Val  Tyr  Lys  Gln  Tyr  Glu  Asp  Met  Val  Val
          115                      120                      125

Glu  Ser  Cys  Gly  Cys  Arg
     130
```

( 2 ) INFORMATION FOR SEQ ID NO:7:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: GDF-6 (C-terminal)

( i x ) FEATURE:
        ( A ) NAME/KEY: Protein
        ( B ) LOCATION: 1..119

( x i ) SEQUENCE DESCRIPTION: SEQ ID NO:7:

```
Ala  Phe  Ala  Ser  Arg  His  Gly  Lys  Arg  His  Gly  Lys  Lys  Ser  Arg  Leu
1                   5                        10                      15

Arg  Cys  Ser  Arg  Lys  Pro  Leu  His  Val  Asn  Phe  Lys  Glu  Leu  Gly  Trp
               20                       25                       30

Asp  Asp  Trp  Ile  Ile  Ala  Pro  Leu  Glu  Tyr  Glu  Ala  Tyr  His  Cys  Glu
               35                       40                       45

Gly  Val  Cys  Asp  Phe  Pro  Leu  Arg  Ser  His  Leu  Glu  Pro  Thr  Asn  His
          50                       55                       60

Ala  Ile  Ile  Gln  Thr  Leu  Met  Asn  Ser  Met  Asp  Pro  Gly  Ser  Thr  Pro
65                       70                       75                       80

Pro  Ser  Cys  Cys  Val  Pro  Thr  Lys  Leu  Thr  Pro  Ile  Ser  Ile  Leu  Tyr
                    85                       90                       95

Ile  Asp  Ala  Gly  Asn  Asn  Val  Val  Tyr  Lys  Gln  Tyr  Glu  Asp  Met  Val
               100                      105                      110

Val  Glu  Ser  Cys  Gly  Cys  Arg
               115
```

( 2 ) INFORMATION FOR SEQ ID NO:8:

( i ) SEQUENCE CHARACTERISTICS:
        ( A ) LENGTH: 123 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: GDF-1

( i x ) FEATURE:
    ( A ) NAME/KEY: Protein
    ( B ) LOCATION: 1..123

( x i ) SEQUENCE DESCRIPTION: SEQ ID NO:8:

| Arg | Pro | Arg | Arg | Asp | Ala | Glu | Pro | Val | Leu | Gly | Gly | Gly | Pro | Gly | Gly |
|---|---|---|---|---|---|---|---|---|---|---|---|---|---|---|---|
| 1 | | | | 5 | | | | | 10 | | | | | 15 | |
| Ala | Cys | Arg | Ala | Arg | Arg | Leu | Tyr | Val | Ser | Phe | Arg | Glu | Val | Gly | Trp |
| | | | 20 | | | | 25 | | | | | 30 | | | |
| His | Arg | Trp | Val | Ile | Ala | Pro | Arg | Gly | Phe | Leu | Ala | Asn | Tyr | Cys | Gln |
| | | 35 | | | | | 40 | | | | | 45 | | | |
| Gly | Gln | Cys | Ala | Leu | Pro | Val | Ala | Leu | Ser | Gly | Ser | Gly | Gly | Pro | Pro |
| | 50 | | | | | 55 | | | | | 60 | | | | |
| Ala | Leu | Asn | His | Ala | Val | Leu | Arg | Ala | Leu | Met | His | Ala | Ala | Ala | Pro |
| 65 | | | | | 70 | | | | | 75 | | | | | 80 |
| Gly | Ala | Ala | Asp | Leu | Pro | Cys | Cys | Val | Pro | Ala | Arg | Leu | Ser | Pro | Ile |
| | | | | 85 | | | | | 90 | | | | | 95 | |
| Ser | Val | Leu | Phe | Phe | Asp | Asn | Ser | Asp | Asn | Val | Val | Leu | Arg | Gln | Tyr |
| | | | 100 | | | | | 105 | | | | | 110 | | |
| Glu | Asp | Met | Val | Val | Asp | Glu | Cys | Gly | Cys | Arg | | | | | |
| | | 115 | | | | | 120 | | | | | | | | |

( 2 ) INFORMATION FOR SEQ ID NO:9:

( i ) SEQUENCE CHARACTERISTICS:
        ( A ) LENGTH: 118 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: BMP-2

( i x ) FEATURE:
        ( A ) NAME/KEY: Protein
        ( B ) LOCATION: 1..118

( x i ) SEQUENCE DESCRIPTION: SEQ ID NO:9:

| Arg | Glu | Lys | Arg | Gln | Ala | Lys | His | Lys | Gln | Arg | Lys | Arg | Leu | Lys | Ser |
|---|---|---|---|---|---|---|---|---|---|---|---|---|---|---|---|
| 1 | | | | 5 | | | | | 10 | | | | | 15 | |
| Ser | Cys | Lys | Arg | His | Pro | Leu | Tyr | Val | Asp | Phe | Ser | Asp | Val | Gly | Trp |
| | | | 20 | | | | 25 | | | | | 30 | | | |
| Asn | Asp | Trp | Ile | Val | Ala | Pro | Pro | Gly | Tyr | His | Ala | Phe | Tyr | Cys | His |
| | | | 35 | | | | | 40 | | | | | 45 | | |
| Gly | Glu | Cys | Pro | Phe | Pro | Leu | Ala | Asp | His | Leu | Asn | Ser | Thr | Asn | His |
| | 50 | | | | | 55 | | | | | 60 | | | | |
| Ala | Ile | Val | Gln | Thr | Leu | Val | Asn | Ser | Val | Asn | Ser | Lys | Ile | Pro | Lys |
| 65 | | | | | 70 | | | | | 75 | | | | | 80 |
| Ala | Cys | Cys | Val | Pro | Thr | Glu | Leu | Ser | Ala | Ile | Ser | Met | Leu | Tyr | Leu |
| | | | | 85 | | | | | 90 | | | | | 95 | |
| Asp | Glu | Asn | Glu | Lys | Val | Val | Leu | Lys | Asn | Tyr | Gln | Asp | Met | Val | Val |
| | | | | 100 | | | | | 105 | | | | | 110 | |
| Glu | Gly | Cys | Gly | Cys | Arg | | | | | | | | | | |
| | | 115 | | | | | | | | | | | | | |

( 2 ) INFORMATION FOR SEQ ID NO:10:

( i ) SEQUENCE CHARACTERISTICS:
        ( A ) LENGTH: 118 amino acids
        ( B ) TYPE: amino acid (C) STRANDEDNESS: single
(D) TOPOLOGY: linear (ii) MOLECULE TYPE: protein (vii) IMMEDIATE SOURCE:
(B) CLONE: BMP-4

(ix) FEATURE:
(A) NAME/KEY: Protein
(B) LOCATION: 1..118

(xi) SEQUENCE DESCRIPTION: SEQ ID NO:10:

```
Lys Arg Ser Pro Lys His His Ser Gln Arg Ala Arg Lys Lys Asn Lys
 1               5                  10                  15
Asn Cys Arg Arg His Ser Leu Tyr Val Asp Phe Ser Asp Val Gly Trp
             20                  25                  30
Asn Asp Trp Ile Val Ala Pro Pro Gly Tyr Gln Ala Phe Tyr Cys His
             35                  40                  45
Gly Asp Cys Pro Phe Pro Leu Ala Asp His Leu Asn Ser Thr Asn His
             50                  55                  60
Ala Ile Val Gln Thr Leu Val Asn Ser Val Asn Ser Ser Ile Pro Lys
 65                  70                  75                  80
Ala Cys Cys Val Pro Thr Glu Leu Ser Ala Ile Ser Met Leu Tyr Leu
                 85                  90                  95
Asp Glu Tyr Asp Lys Val Val Leu Lys Asn Tyr Gln Glu Met Val Val
                100                 105                 110
Glu Gly Cys Gly Cys Arg
                115
```

(2) INFORMATION FOR SEQ ID NO:11:

(i) SEQUENCE CHARACTERISTICS:
(A) LENGTH: 119 amino acids
(B) TYPE: amino acid
(C) STRANDEDNESS: single
(D) TOPOLOGY: linear (ii) MOLECULE TYPE: protein (vii) IMMEDIATE SOURCE:
(B) CLONE: Vgr-1

(ix) FEATURE:
(A) NAME/KEY: Protein
(B) LOCATION: 1..119

(xi) SEQUENCE DESCRIPTION: SEQ ID NO:11:

```
Ser Arg Gly Ser Gly Ser Ser Asp Tyr Asn Gly Ser Glu Leu Lys Thr
 1               5                  10                  15
Ala Cys Lys Lys His Glu Leu Tyr Val Ser Phe Gln Asp Leu Gly Trp
             20                  25                  30
Gln Asp Trp Ile Ile Ala Pro Lys Gly Tyr Ala Ala Asn Tyr Cys Asp
             35                  40                  45
Gly Glu Cys Ser Phe Pro Leu Asn Ala His Met Asn Ala Thr Asn His
             50                  55                  60
Ala Ile Val Gln Thr Leu Val His Leu Met Asn Pro Glu Tyr Val Pro
 65                  70                  75                  80
Lys Pro Cys Cys Ala Pro Thr Lys Leu Asn Ala Ile Ser Val Leu Tyr
                 85                  90                  95
Phe Asp Asp Asn Ser Asn Val Ile Leu Lys Lys Tyr Arg Asn Met Val
                100                 105                 110
Val Arg Ala Cys Gly Cys His
```

115

( 2 ) INFORMATION FOR SEQ ID NO:12:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: OP-1

( i x ) FEATURE:
        ( A ) NAME/KEY: Protein
        ( B ) LOCATION: 1..119

( x i ) SEQUENCE DESCRIPTION: SEQ ID NO:12:

```
Leu  Arg  Met  Ala  Asn  Val  Ala  Glu  Asn  Ser  Ser  Asp  Gln  Arg  Gln
1              5                        10                       15

Ala  Cys  Lys  Lys  His  Glu  Leu  Tyr  Val  Ser  Phe  Arg  Asp  Leu  Gly  Trp
               20                       25                       30

Gln  Asp  Trp  Ile  Ile  Ala  Pro  Glu  Gly  Tyr  Ala  Ala  Tyr  Tyr  Cys  Glu
          35                       40                       45

Gly  Glu  Cys  Ala  Phe  Pro  Leu  Asn  Ser  Tyr  Met  Asn  Ala  Thr  Asn  His
          50                       55                       60

Ala  Ile  Val  Gln  Thr  Leu  Val  His  Phe  Ile  Asn  Pro  Glu  Thr  Val  Pro
65                       70                       75                       80

Lys  Pro  Cys  Cys  Ala  Pro  Thr  Gln  Leu  Asn  Ala  Ile  Ser  Val  Leu  Tyr
                    85                       90                       95

Phe  Asp  Asp  Ser  Ser  Asn  Val  Ile  Leu  Lys  Lys  Tyr  Arg  Asn  Met  Val
               100                      105                      110

Val  Arg  Ala  Cys  Gly  Cys  His
               115
```

( 2 ) INFORMATION FOR SEQ ID NO:13:

( i ) SEQUENCE CHARACTERISTICS:
        ( A ) LENGTH: 119 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: BMP-5

( i x ) FEATURE:
        ( A ) NAME/KEY: Protein
        ( B ) LOCATION: 1..119

( x i ) SEQUENCE DESCRIPTION: SEQ ID NO:13:

```
Ser  Arg  Met  Ser  Ser  Val  Gly  Asp  Tyr  Asn  Thr  Ser  Glu  Gln  Lys  Gln
1              5                        10                       15

Ala  Cys  Lys  Lys  His  Glu  Leu  Tyr  Val  Ser  Phe  Arg  Asp  Leu  Gly  Trp
               20                       25                       30

Gln  Asp  Trp  Ile  Ile  Ala  Pro  Glu  Gly  Tyr  Ala  Ala  Phe  Tyr  Cys  Asp
          35                       40                       45

Gly  Glu  Cys  Ser  Phe  Pro  Leu  Asn  Ala  His  Met  Asn  Ala  Thr  Asn  His
          50                       55                       60

Ala  Ile  Val  Gln  Thr  Leu  Val  His  Leu  Met  Phe  Pro  Asp  His  Val  Pro
65                       70                       75                       80
```

```
            Lys  Pro  Cys  Cys  Ala  Pro  Thr  Lys  Leu  Asn  Ala  Ile  Ser  Val  Leu  Tyr
                           85                       90                       95

Phe  Asp  Asp  Ser  Ser  Asn  Val  Ile  Leu  Lys  Lys  Tyr  Arg  Asn  Met  Val
                          100                      105                     110

Val  Arg  Ser  Cys  Gly  Cys  His
                          115
```

( 2 ) INFORMATION FOR SEQ ID NO:14:

( i ) SEQUENCE CHARACTERISTICS:
        ( A ) LENGTH: 120 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: BMP-3

( i x ) FEATURE:
        ( A ) NAME/KEY: Protein
        ( B ) LOCATION: 1..120

( x i ) SEQUENCE DESCRIPTION: SEQ ID NO:14:

```
            Glu  Gln  Thr  Leu  Lys  Lys  Ala  Arg  Arg  Lys  Gln  Trp  Ile  Glu  Pro  Arg
            1                  5                       10                      15

Asn  Cys  Ala  Arg  Arg  Tyr  Leu  Lys  Val  Asp  Phe  Ala  Asp  Ile  Gly  Trp
                           20                      25                      30

Ser  Glu  Trp  Ile  Ile  Ser  Pro  Lys  Ser  Phe  Asp  Ala  Tyr  Tyr  Cys  Ser
                           35                      40                      45

Gly  Ala  Cys  Gln  Phe  Pro  Met  Pro  Lys  Ser  Leu  Lys  Pro  Ser  Asn  His
                           50                      55                      60

Ala  Thr  Ile  Gln  Ser  Ile  Val  Arg  Ala  Val  Gly  Val  Val  Pro  Gly  Ile
            65                           70                      75                      80

Pro  Glu  Pro  Cys  Cys  Val  Pro  Glu  Lys  Met  Ser  Ser  Leu  Ser  Ile  Leu
                           85                      90                      95

Phe  Phe  Asp  Glu  Asn  Lys  Asn  Val  Val  Leu  Lys  Val  Tyr  Pro  Asn  Met
                          100                     105                     110

Thr  Val  Glu  Ser  Cys  Ala  Cys  Arg
                          115                     120
```

( 2 ) INFORMATION FOR SEQ ID NO:15:

( i ) SEQUENCE CHARACTERISTICS:
        ( A ) LENGTH: 116 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: MIS ( i x ) FEATURE:
        ( A ) NAME/KEY: Protein
        ( B ) LOCATION: 1..116

( x i ) SEQUENCE DESCRIPTION: SEQ ID NO:15:

```
            Gly  Pro  Gly  Arg  Ala  Gln  Arg  Ser  Ala  Gly  Ala  Thr  Ala  Ala  Asp  Gly
            1                  5                       10                      15

Pro  Cys  Ala  Leu  Arg  Glu  Leu  Ser  Val  Asp  Leu  Arg  Ala  Glu  Arg  Ser
                           20                      25                      30
```

-continued

```
Val  Leu  Ile  Pro  Glu  Thr  Tyr  Gln  Ala  Asn  Asn  Cys  Gln  Gly  Val  Cys
          35                       40                      45

Gly  Trp  Pro  Gln  Ser  Asp  Arg  Asn  Pro  Arg  Tyr  Gly  Asn  His  Val  Val
     50                       55                           60

Leu  Leu  Leu  Lys  Met  Gln  Ala  Arg  Gly  Ala  Ala  Leu  Ala  Arg  Pro  Pro
65                       70                       75                        80

Cys  Cys  Val  Pro  Thr  Ala  Tyr  Ala  Gly  Lys  Leu  Leu  Ile  Ser  Leu  Ser
               85                       90                            95

Glu  Glu  Arg  Ile  Ser  Ala  His  His  Val  Pro  Asn  Met  Val  Ala  Thr  Glu
               100                      105                     110

Cys  Gly  Cys  Arg
               115
```

( 2 ) INFORMATION FOR SEQ ID NO:16:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Inhibin-alpha ( i x ) FEATURE:
        ( A ) NAME/KEY: Protein
        ( B ) LOCATION: 1..122

( x i ) SEQUENCE DESCRIPTION: SEQ ID NO:16:

```
Ala  Leu  Arg  Leu  Leu  Gln  Arg  Pro  Pro  Glu  Glu  Pro  Ala  Ala  His  Ala
1                   5                        10                      15

Asn  Cys  His  Arg  Val  Ala  Leu  Asn  Ile  Ser  Phe  Gln  Glu  Leu  Gly  Trp
               20                       25                      30

Glu  Arg  Trp  Ile  Val  Tyr  Pro  Pro  Ser  Phe  Ile  Phe  His  Tyr  Cys  His
               35                       40                      45

Gly  Gly  Cys  Gly  Leu  His  Ile  Pro  Pro  Asn  Leu  Ser  Leu  Pro  Val  Pro
     50                       55                      60

Gly  Ala  Pro  Pro  Thr  Pro  Ala  Gln  Pro  Tyr  Ser  Leu  Leu  Pro  Gly  Ala
65                       70                       75                        80

Gln  Pro  Cys  Cys  Ala  Ala  Leu  Pro  Gly  Thr  Met  Arg  Pro  Leu  His  Val
               85                       90                           95

Arg  Thr  Thr  Ser  Asp  Gly  Gly  Tyr  Ser  Phe  Lys  Tyr  Glu  Thr  Val  Pro
               100                      105                     110

Asn  Leu  Leu  Thr  Gln  His  Cys  Ala  Cys  Ile
               115                      120
```

( 2 ) INFORMATION FOR SEQ ID NO:17:

( i ) SEQUENCE CHARACTERISTICS:
        ( A ) LENGTH: 122 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Inhibin-beta-alpha ( i x ) FEATURE:
        ( A ) NAME/KEY: Protein
        ( B ) LOCATION: 1..122

( x i ) SEQUENCE DESCRIPTION: SEQ ID NO:17:

```
His  Arg  Arg  Arg  Arg  Arg  Gly  Leu  Glu  Cys  Asp  Gly  Lys  Val  Asn  Ile
 1                 5                        10                       15

Cys  Cys  Lys  Lys  Gln  Phe  Phe  Val  Ser  Phe  Lys  Asp  Ile  Gly  Trp  Asn
                20                       25                       30

Asp  Trp  Ile  Ile  Ala  Pro  Ser  Gly  Tyr  His  Ala  Asn  Tyr  Cys  Glu  Gly
           35                       40                       45

Glu  Cys  Pro  Ser  His  Ile  Ala  Gly  Thr  Ser  Gly  Ser  Ser  Leu  Ser  Phe
      50                       55                       60

His  Ser  Thr  Val  Ile  Asn  His  Tyr  Arg  Met  Arg  Gly  His  Ser  Pro  Phe
 65                      70                       75                            80

Ala  Asn  Leu  Lys  Ser  Cys  Cys  Val  Pro  Thr  Lys  Leu  Arg  Pro  Met  Ser
                85                       90                            95

Met  Leu  Tyr  Tyr  Asp  Asp  Gly  Gln  Asn  Ile  Ile  Lys  Lys  Asp  Ile  Gln
               100                      105                      110

Asn  Met  Ile  Val  Glu  Glu  Cys  Gly  Cys  Ser
               115                      120
```

( 2 ) INFORMATION FOR SEQ ID NO:18:

( i ) SEQUENCE CHARACTERISTICS:
        ( A ) LENGTH: 121 amino acids
        ( B ) TYPE: amino acid
        ( C ) STRANDEDNESS: single
        ( D ) TOPOLOGY: linear ( i i ) MOLECULE TYPE: protein ( v i i ) IMMEDIATE SOURCE:
        ( B ) CLONE: Inhibin-beta-beta ( i x ) FEATURE:
        ( A ) NAME/KEY: Protein
        ( B ) LOCATION: 1..121

( x i ) SEQUENCE DESCRIPTION: SEQ ID NO:18:

```
His  Arg  Ile  Arg  Lys  Arg  Gly  Leu  Glu  Cys  Asp  Gly  Arg  Thr  Asn  Leu
 1                 5                        10                       15

Cys  Cys  Arg  Gln  Gln  Phe  Phe  Ile  Asp  Phe  Arg  Leu  Ile  Gly  Trp  Asn
                20                       25                       30

Asp  Trp  Ile  Ile  Ala  Pro  Thr  Gly  Tyr  Tyr  Gly  Asn  Tyr  Cys  Glu  Gly
           35                       40                       45

Ser  Cys  Pro  Ala  Tyr  Leu  Ala  Gly  Val  Pro  Gly  Ser  Ala  Ser  Ser  Phe
      50                       55                       60

His  Thr  Ala  Val  Val  Asn  Gln  Tyr  Arg  Met  Arg  Gly  Leu  Asn  Pro  Gly
 65                      70                       75                            80

Thr  Val  Asn  Ser  Cys  Cys  Ile  Pro  Thr  Lys  Leu  Ser  Thr  Met  Ser  Met
                85                       90                            95

Leu  Tyr  Phe  Asp  Asp  Glu  Tyr  Asn  Ile  Val  Lys  Arg  Asp  Val  Pro  Asn
               100                      105                      110

Met  Ile  Val  Glu  Glu  Cys  Gly  Cys  Ala
               115                      120
```

( 2 ) INFORMATION FOR SEQ ID NO:19:

( i ) SEQUENCE CHARACTERISTICS:
        ( A ) LENGTH: 115 amino acids
        ( B ) TYPE: amino acid
        ( C ) STRANDEDNESS: single
        ( D ) TOPOLOGY: linear ( i i ) MOLECULE TYPE: protein (vii) IMMEDIATE SOURCE:
  (B) CLONE: TGF-beta-1

(ix) FEATURE:
  (A) NAME/KEY: Protein
  (B) LOCATION: 1..115

(xi) SEQUENCE DESCRIPTION: SEQ ID NO:19:

```
His Arg Arg Ala Leu Asp Thr Asn Tyr Cys Phe Ser Ser Thr Glu Lys
1               5                   10                  15

Asn Cys Cys Val Arg Gln Leu Tyr Ile Asp Phe Arg Lys Asp Leu Gly
                20                  25                  30

Trp Lys Trp Ile His Glu Pro Lys Gly Tyr His Ala Asn Phe Cys Leu
            35                  40                  45

Gly Pro Cys Pro Tyr Ile Trp Ser Leu Asp Thr Gln Tyr Ser Lys Val
        50                  55                  60

Leu Ala Leu Tyr Asn Gln His Asn Pro Gly Ala Ser Ala Ala Pro Cys
65                  70                  75                  80

Cys Val Pro Gln Ala Leu Glu Pro Leu Pro Ile Val Tyr Tyr Val Gly
                85                  90                  95

Arg Lys Pro Lys Val Glu Gln Leu Ser Asn Met Ile Val Arg Ser Cys
                100                 105                 110

Lys Cys Ser
        115
```

(2) INFORMATION FOR SEQ ID NO:20:

(i) SEQUENCE CHARACTERISTICS:
    (A) LENGTH: 115 amino acids
    (B) TYPE: amino acid
    (C) STRANDEDNESS: single
    (D) TOPOLOGY: linear (ii) MOLECULE TYPE: protein (vii) IMMEDIATE SOURCE:
    (B) CLONE: TGF-beta-2

(ix) FEATURE:
    (A) NAME/KEY: Protein
    (B) LOCATION: 1..115

(xi) SEQUENCE DESCRIPTION: SEQ ID NO:20:

```
Lys Lys Arg Ala Leu Asp Ala Ala Tyr Cys Phe Arg Asn Val Gln Asp
1               5                   10                  15

Asn Cys Cys Leu Arg Pro Leu Tyr Ile Asp Phe Lys Arg Asp Leu Gly
                20                  25                  30

Trp Lys Trp Ile His Glu Pro Lys Gly Tyr Asn Ala Asn Phe Cys Ala
            35                  40                  45

Gly Ala Cys Pro Tyr Leu Trp Ser Ser Asp Thr Gln His Ser Arg Val
        50                  55                  60

Leu Ser Leu Tyr Asn Thr Ile Asn Pro Glu Ala Ser Ala Ser Pro Cys
65                  70                  75                  80

Cys Val Ser Gln Asp Leu Glu Pro Leu Thr Ile Leu Tyr Tyr Ile Gly
                85                  90                  95

Lys Thr Pro Lys Ile Glu Gln Leu Ser Asn Met Ile Val Lys Ser Cys
                100                 105                 110

Lys Cys Ser
        115
```

(2) INFORMATION FOR SEQ ID NO:21:

(i) SEQUENCE CHARACTERISTICS:
  (A) LENGTH: 115 amino acids
  (B) TYPE: amino acid
  (C) STRANDEDNESS: single
  (D) TOPOLOGY: linear (ii) MOLECULE TYPE: protein (vii) IMMEDIATE SOURCE:
  (B) CLONE: TGF-beta-3

(ix) FEATURE:
  (A) NAME/KEY: Protein
  (B) LOCATION: 1..115

(xi) SEQUENCE DESCRIPTION: SEQ ID NO:21:

```
Lys Lys Arg Ala Leu Asp Thr Asn Tyr Cys Phe Arg Asn Leu Glu Glu
 1               5                  10                  15
Asn Cys Cys Val Arg Pro Leu Tyr Ile Asp Phe Arg Gln Asp Leu Gly
            20                  25                  30
Trp Lys Trp Val His Glu Pro Lys Gly Tyr Tyr Ala Asn Phe Cys Ser
        35                  40                  45
Gly Pro Cys Pro Tyr Leu Arg Ser Ala Asp Thr Thr His Ser Thr Val
    50                  55                  60
Leu Gly Leu Tyr Asn Thr Leu Asn Pro Glu Ala Ser Ala Ser Pro Cys
65                  70                  75                  80
Cys Val Pro Gln Asp Leu Glu Pro Leu Thr Ile Leu Tyr Tyr Val Gly
                85                  90                  95
Arg Thr Pro Lys Val Glu Gln Leu Ser Asn Met Val Val Lys Ser Cys
            100                 105                 110
Lys Cys Ser
        115
```

GROWTH DIFFERENTIATION FACTOR-6

This application is a 371 application of PCT US94/07762, filed Jul. 8, 1994, which is a continuation of Ser. No. 08/089,300, filed Jul. 9, 1993, now abandoned.

BACKGROUND OF THE INVENTION

1. Field of the Invention

The invention relates generally to growth factors and specifically to a new member of the transforming growth factor beta (TGF-β) superfamily, which is denoted, growth differentiation factor-6 (GDF-6).

2. Description of Related Art

The transforming growth factor β (TGF-p) superfamily encompasses a group of structurally-related proteins which affect a wide range of differentiation processes during embryonic development. The family includes, Mullerian inhibiting substance (MIS), which is required for normal male sex development (Behringer, et al., *Nature*, 345:167, 1990), Drosophila decapentaplegic (DPP) gene product, which is required for dorsal-ventral axis formation and morphogenesis of the imaginal disks (Padgett, et al., *Nature*, 325:81–84, 1987), the Xenopus Vg-1 gene product, which localizes to the vegetal pole of eggs ((Weeks, et al., *Cell*, 51:861–867, 1987), the activins (Mason, et al., *Biochem, Biophys. Res. Commun.*, 135:957–964, 1986), which can induce the formation of mesoderm and anterior structures in *Xenopus* embryos (Thomsen, et al., *Cell*, 63:485, 1990), and the bone morphogenetic proteins (BMPS, osteogenin, OP-1) which can induce de novo cartilage and bone formation (Sampath, et al., *J. Biol. Chem.*, 265:13198, 1990). The TGF-βs can influence a variety of differentiation processes, including adipogenesis, myogenesis, chondrogenesis, hematopoiesis, and epithelial cell differentiation (for review, see Massague, *Cell* 49:437, 1987).

The proteins of the TGF-β family are initially synthesized as a large precursor protein which subsequently undergoes proteolytic cleavage at a cluster of basic residues approximately 110–140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray, A., and Maston, A., *Science*, 247:1328, 1990). Additional studies by Hammonds, et al., (*Molec. Endocrin.* 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling, et al., *Nature*, 321:779, 1986) and the TGF-βs (Cheifetz, et al., *Cell*, 48:409, 1987), heterodimers have also been detected, and these appear to have different biological properties than the respective homodimers.

Identification of new factors that are tissue-specific in their expression pattern will provide a greater understanding of that tissue's development and function.

SUMMARY OF THE INVENTION

The present invention provides a cell growth and differentiation factor, GDF-6, a polynucleotide sequence which encodes the factor, and antibodies which are immunoreactive with the factor. This factor appears to relate to various cell proliferative disorders, especially those involving placental tissue.

Thus, in one embodiment, the invention provides a method for detecting a cell proliferative disorder of placental origin and which is associated with GDF-6. In another embodiment, the invention provides a method for treating a cell proliferative disorder by suppressing or enhancing GDF-6 activity.

BRIEF DESCRIPTION OF THE DRAWINGS

FIG. 2 shows nucleotide and predicted amino acid sequence of murine GDF-6 (SEQ ID NO:5 and SEQ ID NO:6, respectively. The putative pentabasic processing site is boxed.

FIG. 3 shows the alignment of the C-terminal sequences of GDF-6 with other members of the TGF-β superfamily (SEQ ID NOS: 7–21). The conserved cysteine residues are boxed. Dashes denote gaps introduced in order to maximize alignment.

FIG. 4 shows amino acid homologies among different members of the TGF-β superfamily. Numbers represent percent amino acid identities between each pair calculated from the first conserved cysteine to the C-terminus. Boxes represent homologies among highly-related members within particular subgroups.

DETAILED DESCRIPTION OF THE INVENTION

Figure 1:
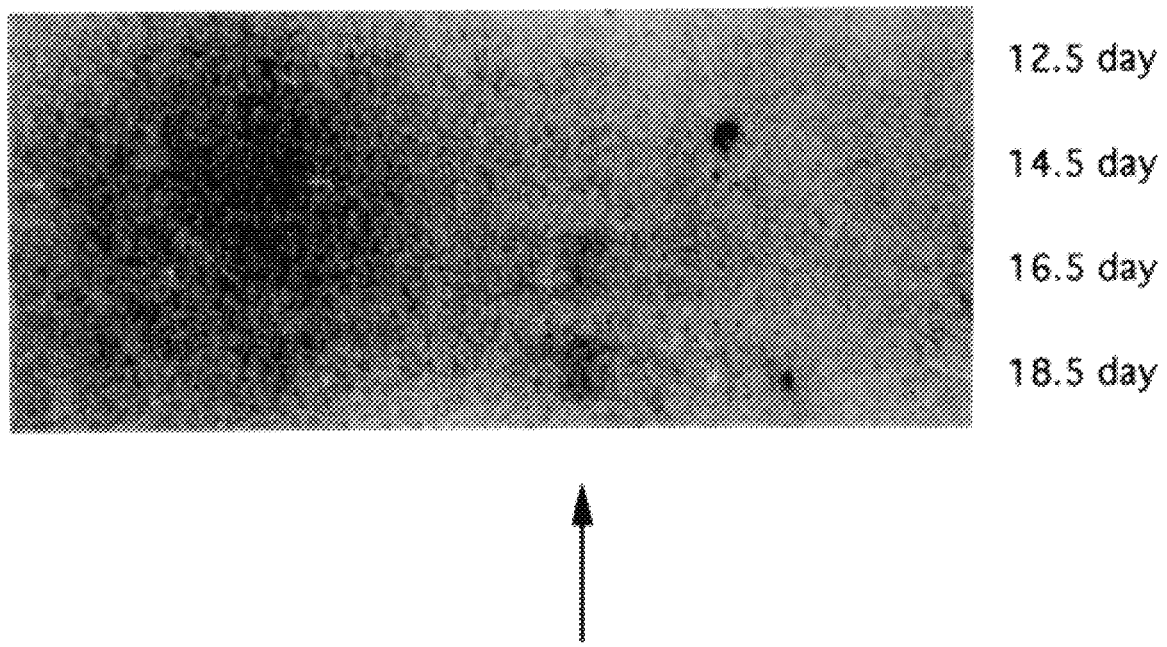
FIG. 1 shows expression of GDF-6 mRNA in placenta. The arrow denotes the position of the major mRNA species.

The present invention provides a growth and differentiation factor, GDF-6 and a polynucleotide sequence encoding GDF-6. GDF-6 is expressed in placental tissue. In one embodiment, the invention provides a method for detection of a cell proliferative disorder of placental origin which is associated with GDF-6 expression. In another embodiment, the invention provides a method for treating a cell proliferative disorder by using an agent which suppresses or enhances GDF-6 activity.

The TGF-β superfamily consists of multifunctional polypeptides that control proliferation, differentiation, and other functions in many cell types. Many of the peptides have regulatory, both positive and negative, effects on other peptide growth factors. The structural homology between the GDF-6 protein of this invention and the members of the TGF-β family, indicates that GDF-6 is a new member of the family of growth and differentiation factors. Based on the known activities of many of the other members, it can be expected that GDF-6 will also possess biological activities that will make it useful as a diagnostic and therapeutic reagent.

The expression of GDF-6 in the placenta suggests a variety of applications using the polypeptide, polynucleotide, and antibodies of the invention, related to pregnancy and cell proliferative diseases. Abnormally low levels of the factor may be indicative of impaired function in the placenta while abnormally high levels may be indicative of hypertrophy or hyperplasia. Hence, GDF-6 may be useful in detecting primary and metastic neoplasms of placental origin. In addition, GDF-6 may also be useful as an indicator of developmental anomalies in prenatal screening procedures.

Several members of the TGF-β superfamily possess activities suggesting possible applications for the treatment of cell proliferative disorders, such as cancer. In particular, TGF-β has been shown to be potent growth inhibitor for a variety of cell types (Massague, *Cell,* 49:437, 1987). MIS has been shown to inhibit the growth of human endometrial carcinoma tumors in nude mice (Donahoe, et al., *Ann. Surg.,* 194:472, 1981), and inhibin α has been shown to suppress the development of tumors both in the ovary and in the testis (Matzuk, et al., *Nature,* 360:313, 1992) GDF-6 may have a simlar actiity and may therefore be useful as an antiproliferative agent, such as for the treatment choriocarcinoma.

Many of the members of the TGF-β family are also important mediators of tissue repair. TGF-β has been shown to have marked effects on the formation of collagen and causes of striking angiogenic response in teh newborn mouse (roberts, et al., *Proc. Natl. acad. Sci.,* USA, 83:4167, 1986). The BMP's can induce new bone growth and are effective for the treatment of fractures and other skeletal defects (Glowacki, et al., *Lancet,* 1:959, 1981; Ferguson, et al., *Clin. Orthoped. Relat. Res.,,* 227:265, 1988; Johnson, et al., *Clin Orthoped. Relat. Res.,* 230:257, 1988). GDF-6 may have simlar activities and may be useful in repair of tissue injury caused by trauma or burns for example.

GDF-6 may play a role in the regulation of uterine function during pregmancy, and therefore, GDF-6, anti-GDF-6 antibodies, or antisense polynucleotides may be useful in preventing premature labor.

The term "substantially pure" as used herein refers to GDF-6 which is substantially free of other proteins, lipids, carbohydrates or other materials with which it is naturally associated. One skilled in the art can purify GDF-6 using standard techniques for protein purification. The substantially pure polypeptide will yield a single major band on a non-reducing polyacrylamide gel. The purity of the GDF-6 polypeptide can also be determined by amino-terminal amino acid sequence analysis. GDF-6 polypeptide includes functional fragments of the polypeptide, as long as the activity of GDF-7 remains. Smaller peptides containing the biological activity of GDF-7 are included in the invention.

The invention provides polynucleotides encoding the GDF-6 protein. These polynucleotides include DNA, cDNA and RNA sequences which encode GDF-6. It is understood that all polynucleotides encoding all or a portion of GDF-6 are also included herein, as long as they encode a polypeptide with GDF-6 activity. Such polynucleotides include naturally occurring, synthetic, and intentionally manipulated polynucleotides. For example, GDF-6 polynucleotide may be subjected to site-directed mutagenesis. The polynucleotide sequence for GDF-6 also includes antisense sequences. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of GDF-6 polypeptide encoded by the nucleotide sequence is functionally unchanged.

Specifically disclosed herein is a genomic DNA sequence containing a portion of the GDF-6 gene. The sequence contains an open reading frame corresponding to the predicted C-terminal region of the GDF-6 precursor protein. The encoded polypeptide is predicted to contain a potential pentabasic proteolytic processing site. Cleavage of the precursor at this site would generate a mature biologically active C-terminal fragment of 120 amino acids with a predicted molecular weight of approximately 13,600.

The C-terminal region of GDF-6 following the putative proteolytic processing site shows significant homology to the known members of the TGF-β superfamily. The GDF-6 sequence contains most of the residues that are highly conserved in other family members (see FIG. 3). Among the known family members, GDF-6 is most homologous to BMP-2 (57% sequence identity) (see FIG. 4).

Minor modifications of the recombinant GDF-6 primary amino acid sequence may result in proteins which have substantially equivalent activity as compared to the GDF-6 polypeptide described herein. Such modifications may be deliberate, as by site-directed mutagenesis, or may be spontaneous. All of the polypeptides produced by these modifications are included herein as long as the biological activity of GDF-6 still exists. Further, deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for GDF-6 biological activity.

The nucleotide sequence encoding the GDF-6 polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences of the invention can be obtained by several methods. For example, the DNA can be isolated using hybridization techniques which are well known in the art. These include, but are not limited to: 1) hybridization of genomic or cDNA libraries with probes to detect homologous nucleotide sequences, 2) polymerase chain reaction (PCR) on genomic DNA or cDNA using primers capable of annealing to the DNA sequence of interest, and 3) antibody screening of expression libraries to detect cloned DNA fragments with shared structural features.

Preferably the GDF-6 polynucleotide of the invention is derived from a mammalian organism, and most preferably from a mouse, rat, or human. Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.,* 9:879, 1981).

The development of specific DNA sequences encoding GDF-6 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA.

Of the three above-noted methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al., *Nucl. Acid Res.,* 11:2325, 1983).

A cDNA expression library, such as lambda gt11, can be screened indirectly for GDF-6 peptides having at least one epitope, using antibodies specific for GDF-6. Such antibodies can be either polyclonally or monoclonally derived and used to detect expression product indicative of the presence of GDF-6 CDNA.

DNA sequences encoding GDF-6 can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the GDF-6 polynucleotide sequences may be inserted into a recombinant expression vector. The term "recombinant expression vector" refers to a plasmid, virus or other vehicle known in the art that has been manipulated by insertion or incorporation of the GDF-6 genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., *Gene,* 56:125, 1987), the pMSXND expression vector for expression in mammalian cells (Lee and Nathans, *J. Biol. Chem.,* 263:3521, 1988) and baculovirus-derived vectors for expression in insect cells. The DNA segment can be present in the vector operably linked to regulatory elements, for example, a promoter (e.g., T7, metallothionein 1, or polyhedrin promoters).

Polynucleotide sequences encoding GDF-6 can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-6 is expressed from a cDNA clone containing the entire coding sequence of GDF-6. Alternatively, the C-terminal portion of GDF-6 can be expressed as a fusion protein with the pro- region of another member of the TGF-β family or co-expressed with another pro- region (see for example, Hammonds, et al., *Molec. Endocrin.* 5:149, 1991; Gray, A., and Mason, A., *Science,* 247:1328, 1990).

Transformation of a host cell with recombinant DNA may be carried out by conventional techniques as are well known to those skilled in the art. Where the host is prokaryotic, such as *E. coli,* competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the GDF-6 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, *Eukaryotic Viral Vectors,* Cold Spring Harbor Laboratory, Gluzman ed., 1982).

Isolation and purification of microbial expressed polypeptide, or fragments thereof, provided by the invention, may be carried out by conventional means including preparative chromatography and immunological separations involving monoclonal or polyclonal antibodies.

The invention includes antibodies immunoreactive with GDF-6 polypeptide or functional fragments thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., *Nature,* 256:495, 1975). The term antibody as used in this invention is meant to include intact molecules as well as fragments thereof, such as Fab and F(ab')$_2$, which are capable of binding an epitopic determinant on GDF-6.

The term "cell-proliferative disorder" denotes malignant as well as non-malignant cell populations which often appear to differ from the surrounding tissue both morphologically and genotypically. Malignant cells (i.e. cancer) develop as a result of a multistep process. The GDF-6 polynucleotide that is an antisense molecule is useful in treating malignancies of the various organ systems, particularly, for example, cells in placental tissue. Essentially, any disorder which is etiologically linked to altered expression of GDF-6 could be considered susceptible to treatment with a GDF-6 suppressing reagent. One such disorder is a malignant cell proliferative disorder, for example.

The invention provides a method for detecting a cell proliferative disorder of placental tissue which comprises contacting an anti-GDF-6 antibody with a cell suspected of having a GDF-6 associated disorder and detecting binding to the antibody. The antibody reactive with GDF-6 is labeled with a compound which allows detection of binding to GDF-6. For purposes of the invention, an antibody specific for GDF-6 polypeptide may be used to detect the level of GDF-6 in biological fluids and tissues. Any specimen containing a detectable amount of antigen can be used. A preferred sample of this invention is placental tissue. The level of GDF-6 in the suspect cell can be compared with the level in a normal cell to determine whether the subject has a GDF-6-associated cell proliferative disorder. Preferably the subject is human.

The antibodies of the invention can be used in any subject in which it is desirable to administer in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and noncompetitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those of ordinary skill in the art will know of other suitable labels for binding to the antibody, or will be able to ascertain such, using routine experimentation.

Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti-hapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. Such dosages may vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140–250 keV range, which may readily be detected by conventional gamma cameras.

For in vivo diagnosis radioisotopes may be bound to immunoglobulin either directly or indirectly by using an intermediate functional group. Intermediate functional groups which often are used to bind radioisotopes which exist as metallic ions to immunoglobulins are the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$AS, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{58}$Fe.

The monoclonal antibodies of the invention can be used in vitro and in vivo to monitor the course of amelioration of a GDF-6-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-6-associated disease is effective. The term "ameliorate" denotes a lessening of the detrimental effect of the GDF-6-associated disease in the subject receiving therapy.

The present invention identifies a nucleotide sequence that can be expressed in an altered manner as compared to expression in a normal cell, therefore it is possible to design appropriate therapeutic or diagnostic techniques directed to this sequence. Thus, where a cell-proliferative disorder is associated with the expression of GDF-6, nucleic acid sequences that interfere with GDF-6 expression at the translational level can be used. This approach utilizes, for example, antisense nucleic acid and ribozymes to block translation of a specific GDF-6 mRNA, either by masking that mRNA with an antisense nucleic acid or by cleaving it with a ribozyme.

Antisense nucleic acids are DNA or RNA molecules that are complementary to at least a portion of a specific mRNA molecule (Weintraub, *Scientific American*, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target GDF-6-producing cell. The use of antisense methods to inhibit the in vitro translation of genes is well known in the art (Marcus-Sakura, *Anal. Biochem.*, 172:289, 1988).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, *J. Amer. Med. Assn.*, 260:3030, 1988). A major advantage of this approach is that, because they are sequence-specific, only mRNAs with particular sequences are inactivated.

There are two basic types of ribozymes namely, tetrahymena-type (Hasselhoff, *Nature*, 334:585, 1988) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

The present invention also provides gene therapy for the treatment of cell proliferative or immunologic disorders which are mediated by GDF-6 protein. Such therapy would achieve its therapeutic effect by introduction of the GDF-6 antisense polynucleotide into cells having the proliferative disorder. Delivery of antisense GDF-6 polynucleotide can be achieved using a recombinant expression vector such as a chimeric virus or a colloidal dispersion system. Especially preferred for therapeutic delivery of antisense sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a GDF-6 sequence of interest into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the GDF-6 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to $\psi$2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-6 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 $\mu$m can encapsulate a substantial percentage of an aqueous buffer containing large macromolecules. RNA, DNA and intact virions can be encapsulated within the aqueous interior and be delivered to cells in a biologically active form (Fraley, et al., *Trends Biochem. Sci.*, 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., *Biotechniques,* 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-6 in placental tissue, there are a variety of applications using the polypeptide, polynucleotide, and antibodies of the invention, related to this tissue. Such applications include treatment of cell proliferative disorders involving this tissue. In addition, GDF-6 may be useful in various gene therapy procedures.

The following examples are intended to illustrate but not limit the invention. While they are typical of those that might be used, other procedures known to those skilled in the art may alternatively be used.

EXAMPLE 1

IDENTIFICATION AND ISOLATION OF A NOVEL TGF-β FAMILY MEMBER

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual *E. coli* colonies carrying these subcloned inserts, and using a combination of random sequencing and hybridization analysis to eliminate known members of the superfamily.

GDF-6 was identified from a mixture of PCR products obtained with the primers

SJL141: 5'-CCGGAATTCGGITGG(G/C/A)A(G/A/T/C)(A/G)A(T/C)TGG(A/G)TI (A/G)TI(T/G)CICC-3' (SEO ID NO:1)

SJL1 45:5'-CCGGAATC(G/A)CAI(G/C)C(G/A)CAIG (C/A)(G/A/T/C)TCIACI(G/A) T/C)CAT-3' (SEQ ID NO:2)

PCR using these primers was carried out with 2 pg mouse genomic DNA at 94° C. for 1 min, 50° C. for 2 min, and 72° C. for 2 min for 40 cycles.

PCR products of approximately 280 bp were gel-purified, digested with Eco RI, gel-purified again, and subcloned in the Bluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

The primer combination of SJL141 and SJL145, encoding the amino acid sequences GW(H/Q/N/K/D/E)(D/N)W(V/I/M)(V/I/M)(A/S)P (SEQ ID NO:3) and M(V/I/M/T/A)V(D/E)(A/S)C(G/A)C (SEQ ID NO:4) respectively, yielded four previously identified sequences (BMP-4, inhibin βB, GDF-3 and GDF-5) and two novel sequences, which were designated GDF-6 and GDF-7 among 134 subclones analyzed.

EXAMPLE 2

EXPRESSION PATTERN AND SEQUENCE OF GDF-6

To determine the expression pattern of GDF-6, RNA samples prepared from a variety of adult tissues were screened by Northern analysis. RNA isolation and Northern analysis were carried out as described previously (Lee, S.-J., *Mol. Endocrinol.,* 4:1034, 1990) except that hybridization was carried out in 5X SSPE, 10% dextran sulfate, 50% formamide, 1% SDS, 200 µg/ml salmon DNA, and 0.1% each of bovine serum albumin, ficoll, and polyvinylpyrrolidone. Five micrograms of twice poly A-selected RNA were electrophoresed on formaldehyde gels, blotted, and probed with GDF-6. As shown in FIG. 1, the GDF-6 probe detected a single mRNA species expressed in placentas during late gestation.

To obtain a larger segment of the GDF-6 gene, a mouse genomic library was screened with a probe derived from the GDF-6 PCR product. The partial sequence of a GDF-6 genomic clone is shown in FIG. 2*a*. The sequence contains an open reading frame corresponding to the predicted C-terminal region of the GDF-6 precursor protein. The predicted GDF-6 sequence contains a potential proteolytic processing site, which is boxed. Cleavage of the precursor at this site would generate a mature C-terminal fragment 120 amino acids in length with a predicted molecular weight of 13,600.

The C-terminal region of GDF-6 following the putative proteolytic processing site shows significant homology to the known members of the TGF-β superfamily (FIG. 3). FIG. 3 shows the alignment of the C-terminal sequences of GDF-6 with the corresponding regions of human GDF-1

(Lee, *Proc. Natl. Acad. Sci.* USA, 88:4250–4254, 1991), human BMP-2 and 4 (Wozney, et al., *Science,* 242:1528–1534, 1988), human Vgr-1 (Celeste, et al., *Proc. Natl. Acad. Sci.* USA, 87:9843–9847, 1990), human OP-1 (Ozkaynak, et al., EMBO J., 9:2085–2093, 1990), human BMP-5 (Celeste, et al., *Proc. Natl. Acad. Sci.* USA, 87:9843–9847, 1990), human BMP-3 (Wozney, et al., *Science,* 242:1528–1534, 1988), human MIS (Cate, et al., *Cell,* 45:685–698, 1986), human inhibin alpha, βA, and βB (Mason, et al., *Biochem, Biophys. Res. Commun.,* 135:957–964, 1986), human TGF-β1 (Derynck, et al., *Nature,* 316:701–705, 1985), humanTGF-β2 (deMartin, et al., EMBO J., 6:3673–3677, 1987), and human TGF-β3 (ten Dijke, et al., *Proc. Natl. Acad. Sci.* USA, 85:4715–4719, 1988). The conserved cysteine residues are boxed. Dashes denote gaps introduced in order to maximize the alignment.

GDF-6 contains most of the residues that are highly conserved in other family members, including the seven cysteine residues with their characteristic spacing.

FIG. 4 shows the amino acid homologies among the different members of the TGF-β superfamily. Numbers represent percent amino acid identities between each pair calculated from the first conserved cysteine to the C-terminus. Boxes represent homologies among highly-related members within particular subgroups. In this region, GDF-6 is most homologous to BMP-2 (57% sequence identity).

Although the invention has been described with reference to the presently preferred embodiment, it should be understood that various modifications can be made without departing from the spirit of the invention. Accordingly, the invention is limited only by the following claims.

SUMMARY OF SEQUENCES

SEQ ID NO: 1 is the nucleotide sequence for the GDF-6 primer, SJL141.
SEQ ID NO: 2 is the nucleotide sequence for the GDF-6 primer, SJL145.
SEQ ID NO: 3 is the amino acid sequence for the primer, SJL141.
SEQ ID NO: 4 is the amino acid sequence for primer SJL145.
SEQ ID NO: 5 is the nucleotide and deduced amino acid sequence for GDF-6.
SEQ ID NO: 6 is the deduced amino acid sequence for GDF-6.
SEQ ID NO: 7 is the amino acid for the C-terminal sequence of GDF-6.
SEQ ID NO: 8 is the amino acid for the C-terminal sequence of GDF-1.
SEQ ID NO: 9 is the amino acid for the C-terminal sequence of BMP-2.
SEQ ID NO: 10 is the amino acid for the C-terminal sequence of BMP-4.
SEQ ID NO: 11 is the amino acid for the C-terminal sequence of Vgr-1.
SEQ ID NO: 12 is the amino acid for the C-terminal sequence of OP-1.
SEQ ID NO: 13 is the amino acid for the C-terminal sequence of BMP-5.
SEQ ID NO: 14 is the amino acid for the C-terminal sequence of BMP-3.
SEQ ID NO: 15 is the amino acid for the C-terminal sequence of MIS.
SEQ ID NO: 16 is the amino acid for the C-terminal sequence of Inhibin-alpha.
SEQ ID NO: 17 is the amino acid for the C-terminal sequence of Inhibin-beta-alpha.
SEQ ID NO: 18 is the amino acid for the C-terminal sequence of Inhibin-beta-beta.
SEQ ID NO: 19 is the amino acid for the C-terminal sequence of TGF-beta-1.
SEQ ID NO: 20 is the amino acid for the C-terminal sequence of TGF-beta-2.
SEQ ID NO: 21 is the amino acid for the C-terminal sequence of TGF-beta-3.

We claim:

1. Substantially pure growth differentiation factor-6 (GDF-6) having the amino acid sequence as set forth in SEQ ID NO:6.

2. An isolated polynucleotide encoding GDF-6 polypeptide having an amino acid sequence as set forth in SEQ ID NO:6.

3. The polynucleotide of claim 2, wherein the polynucleotide is isolated from a mammalian cell.

4. The polynucleotide of claim 3, wherein the mammalian cell is selected from the group consisting of mouse, rat, and human cell.

5. An expression vector including the polynucleotide of claim 2.

6. The vector of claim 5, wherein the vector is a plasmid.

7. The vector of claim 5, wherein the vector is a viral vector.

8. A host cell containing the vector of claim 5.

9. The host cell of claim 8, wherein the cell is prokaryotic.

10. The host cell of claim 8, wherein the cell is eukaryotic.

11. An isolated polynucleotide selected from the group consisting of:

a) SEQ ID NO:5;

b) SEQ ID NO:5, wherein T can also be U;

c) nucleic sequences complementary to SEQ ID NO:5; and d) fragments of a), b), or c) that are at least 15 bases in length and that will selectively hybridize to genomic DNA which encodes the GDF-6 protein of SEQ ID NO:6.

* * * * *